(12) United States Patent
Kataoka et al.

(10) Patent No.: US 7,737,274 B2
(45) Date of Patent: Jun. 15, 2010

(54) METHODS FOR PRODUCING PHENYLALANINE DERIVATIVES HAVING A QUINAZOLINEDIONE SKELETON AND INTERMEDIATES FOR PRODUCTION THEREOF

(75) Inventors: Noriyasu Kataoka, Kawasaki (JP); Akinori Tatara, Kawasaki (JP); Masanobu Yatagai, Kawasaki (JP); Junko Yamanaka, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 1132 days.

(21) Appl. No.: 11/207,751

(22) Filed: Aug. 22, 2005

(65) Prior Publication Data

US 2006/0009476 A1 Jan. 12, 2006

Related U.S. Application Data

(63) Continuation of application No. PCT/JP2004/001982, filed on Feb. 20, 2004.

(51) Int. Cl.
*A61K 31/517* (2006.01)
*C07D 239/80* (2006.01)
*C07D 239/88* (2006.01)
*C07C 61/08* (2006.01)
*C07C 63/06* (2006.01)
*C07C 229/56* (2006.01)

(52) U.S. Cl. .................. 544/285; 514/266.31
(58) Field of Classification Search ............ 514/266.31; 544/285; 562/437, 439, 458
See application file for complete search history.

(56) References Cited

U.S. PATENT DOCUMENTS

| | | | |
|---|---|---|---|
| 6,492,364 B1 * | 12/2002 | Takahashi et al. | 514/243 |
| 6,610,710 B2 | 8/2003 | Tanaka et al. | |
| 7,105,520 B2 | 9/2006 | Suzuki et al. | |
| 7,153,963 B2 * | 12/2006 | Makino et al. | 544/284 |
| 7,193,108 B2 | 3/2007 | Chiba et al. | |
| 7,250,516 B2 * | 7/2007 | Okuzumi et al. | 546/157 |
| 2003/0149083 A1 | 8/2003 | Tanaka et al. | |
| 2003/0220268 A1 | 11/2003 | Makino et al. | |
| 2003/0220318 A1 | 11/2003 | Suzuki et al. | |
| 2005/0101779 A1 | 5/2005 | Sagi et al. | |
| 2005/0222141 A1 | 10/2005 | Sagi et al. | |
| 2006/0009476 A1 | 1/2006 | Kataoka et al. | |
| 2006/0223836 A1 | 10/2006 | Makino et al. | |
| 2008/0108637 A1 | 5/2008 | Fujita et al. | |
| 2009/0318688 A1 | 12/2009 | Kataoka et al. | |

FOREIGN PATENT DOCUMENTS

| | | |
|---|---|---|
| EP | 1233013 | 8/2002 |
| EP | 1323711 | 7/2003 |
| WO | WO 01/36376 | 5/2001 |
| WO | WO 02/28830 | 4/2002 |
| WO | WO 03/093237 | 11/2003 |

OTHER PUBLICATIONS

S. Makino, et al., "Solid-Phase Synthesis of Quinazoline-2,4-Diones Using SNAR Reaction", Synlett, No. 3, 2001, pp. 333-336.

S.M. Gadekar, et al., "Anthranilamides as Intermediates for 3-Substituted Quinazoline-2,4-Diones", The Chemical Society, Nov. 1964, pp. 4666-4668.
L. Gouilleux, et al., "Solid Phase Synthesis of Chiral 3-Substituted Quinazoline-2,4-Diones", Tetrahedron Letters, vol. 37, No. 39, 1996, pp. 7031-7034.
B. Taub, et al., "3-Substituted 2,4-Quinazolinediones", The Journal of Organic Chemistry, vol. 26, No. 12, Dec. 1961, pp. 5238-5239.
U.S. Appl. No. 11/963,144, filed Dec. 21, 2007, Sagi, et al.
U.S. Appl. No. 11/767,969, filed Jun. 21, 2007, Sagi, et al.
U.S. Appl. No. 11/430,284, filed May 9, 2006, Makino, et al.
U.S. Appl. No. 11/433,589, filed May 15, 2006, Higuchi, et al.
U.S. Appl. No. 11/433,618, filed May 15, 2006, Ogawa, et al.
U.S. Appl. No. 11/441,106, filed May 26, 2006, Takahashi, et al.

* cited by examiner

Primary Examiner—James O Wilson
Assistant Examiner—Tamthom N Truong
(74) Attorney, Agent, or Firm—Oblon, Spivak, McClelland, Maier & Neustadt, L.L.P.

(57) ABSTRACT

The present invention provides a method for producing a phenylalanine derivative(s) having a quinazolinedione ring of formula (5), including steps comprising of
reacting an acylphenylalanine derivative(s) of formula (1) with a carbonyl group-introducing reagent(s) and a derivative(s) of anthranilic acid to form an asymmetric urea intermediate(s);
making the asymmetric urea intermediate(s) into a quinazolinedione compound(s) of formula (4) in the presence of a base(s); and
N-alkylating quinazolinedione ring amide of the obtained quinazolinedione compounds with N-alkylation agents. This production method is an industrially applicable method for producing phenylalanine derivatives having a quinazolinedione skeleton, which are compounds highly useful as drugs having α 4 integrin inhibiting activity. In the formulae (1) and (5), R1 represents a phenyl group having a substituent(s) and the like, R2 represents an alkyl group and the like, R3 represents a dialkylamino group and the like, and R4 represents an alkyl group and the like.

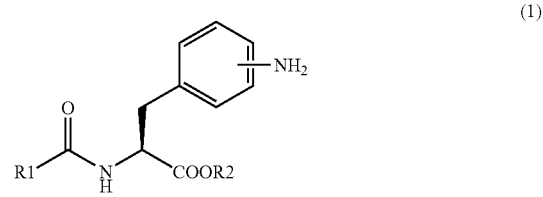

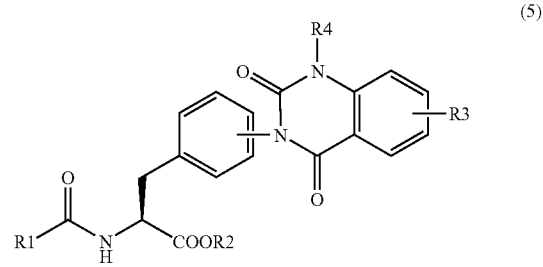

6 Claims, No Drawings

METHODS FOR PRODUCING PHENYLALANINE DERIVATIVES HAVING A QUINAZOLINEDIONE SKELETON AND INTERMEDIATES FOR PRODUCTION THEREOF

BACKGROUND OF THE INVENTION

The present invention relates to methods for producing phenylalanine derivatives having a quinazolinedione skeleton, which are compounds highly useful as drugs having α 4 integrin inhibiting activity, and intermediates thereof.

Recently, research on inflammatory diseases in which α 4 integrin-depending adhesion process participates in the pathology such as rheumatoid arthritis, inflammatory bowel diseases, systemic lupus erythematosus, multiple sclerosis, Sjögren's syndrome, asthma, psoriasis, allergy, diabetes, cardiovascular diseases, arterial sclerosis, restenosis, tumor proliferation, tumor metastasis and transplantation rejection has been advanced, and application to treating or preventing agents of the compounds having α 4 integrin inhibiting activity has been expected.

The applicant has already invented new phenylalanine derivatives having α 4 integrin inhibiting activity, which are highly useful as treating or preventing agents for inflammatory diseases in which α 4 integrin-depending adhesion process participates in the pathology and filed a patent application (WO2002-16329).

Conventionally, as the method for producing the phenylalanine derivatives having a quinazolinedione skeleton, it has been reported such as that a quinazolinedione skeleton is constructed via amide intermediates by supporting phenylalanine derivatives on a solid-phase resin (WO2002-16329 and Synlett, 3, 333-336, 2001).

However, though the solid-phase synthesis method has excellent advantages as synthesis of a wide range of derivatives, generally it is not a method suitable for industrialization because the amount of derivatives which can be supported on a solid-phase resin has limitations and, as a result, the amount of the object substance which can be prepared at one time is extremely small. Further, in the solid-phase synthesis, a reaction reagent(s) is generally excessively used, and this is inappropriate from the point of industrialization.

In addition, by substituting the solid-phase synthesis method with a liquid-phase method based on the solid-phase synthesis method, for example, in accordance with well-known examples of reports (S. M. Gadekar, et al., J. Am. Chem. Soc. 4666-4667, 1964, and L. Gouillex, et al., Tetrahedron lett., 37(39), 7031, 1996), a quinazolinedione skeleton can be constructed by a synthesizing method comprising steps of reacting amine with carboxylic acid of anthranilic acid to form an amide, and reacting an amino group of anthranilic acid with ethyl chloroformate, 1,1'-carbonyldiimidazole or the like to make it in carbamate or carbonylimidazolyl form and then forming a quinazolinedione ring with a base(s). However, when the compound is synthesized, it has problems in that the number of reaction processes are large and therefore the yield is low.

On the other hand, as the method via urea intermediates, it has been known such as that amine is reacted with isocyanate to form an urea and a quinazolinedione ring is formed with a base (for example, WO2002-16329 and B. Taub, J. Org. Chem., 26, 5238-5239, 1961).

However, isocyanate is typically a liquid with a pungent odor and highly toxic, and it is known that isocyanate sometimes induces self-polymerization to produce isocyanurate or reacts with water in the air to disintegrate. Thus, isocyanate is typically low in chemical stability and has toxicity.

From these mentioned above, it is needed to find methods for producing phenylalanine derivatives having a quinazolinedione skeleton suitable for industrialization.

DISCLOSURE OF THE INVENTION

The object of the present invention is to provide industrially applicable methods for producing phenylalanine derivatives having a quinazolinedione skeleton, which are compounds highly useful as drug products having α 4 integrin inhibiting activity.

The present invention also intends to provide intermediates for production of the phenylalanine derivatives having a quinazolinedione skeleton.

The inventors studied the above problems to be solved and they found industrially applicable production methods in which phenylalanine derivatives having a quinazolinedione skeleton are conducted in high yield by a synthesizing method using a carbonyl group-introducing reagent(s) via urea intermediates, which is concise operation in mild reaction temperature without complicated solvent extraction and concentration. The present invention has been completed on the basis of this finding.

[1] Namely, the present invention provides methods for producing phenylalanine derivatives having a quinazolinedione ring of following formula (5), comprising steps of:

reacting an acylphenylalanine derivative(s) of formula (1):

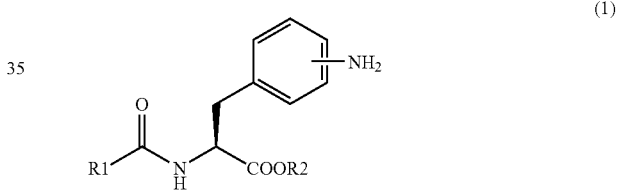

wherein R1 represents a phenyl group which may have a substituent(s) or a pyridyl group which may have a substituent(s), R2 represents an alkyl group which may have a substituent(s), and the derivative(s) is in a salt(s) with chemically acceptable acid(s) or free form(s), with a carbonyl group-introducing reagent(s) and an anthranilic acid derivative(s) of formula (2):

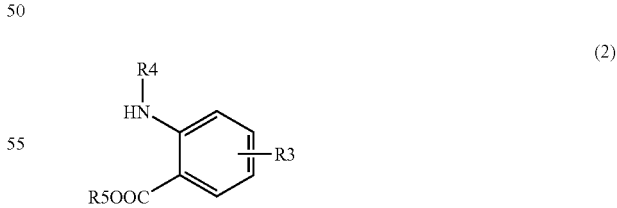

wherein R3 represents a dialkylamino group, a monoalkylamino group, an amino group, a hydrogen atom, a halogen atom, an alkyl group, perfluoroalkyl group, an alkoxy group, a nitro group, an alkyl group substituted with a dialkylamino group, an alkyl group substituted with a monoalkylamino group, an alkyl group substituted with an amino group, an alkyl group substituted with an alkenyl group, an alkyl group substituted with an alkynyl group, a carboxyl group, an alkoxycarbonyl group, an alkylthio group or an arylthio group; R4 represents a hydrogen atom, an alkyl group or a benzyl group which may have a substituent(s); and R5 represents an alkyl group or an alkylcarbonyl group, and the derivative(s) is in a salt(s) with chemically acceptable acid(s) or free form(s), to form an asymmetric urea intermediate(s) of formula (3):

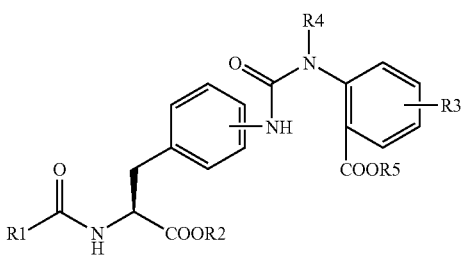

(3)

wherein R1 to R5 are defined above;

making the asymmetric urea intermediate(s) into a quinazolinedione compound(s) of formula (4) in the presence of a base(s):

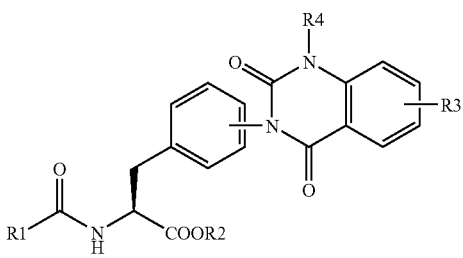

(4)

wherein R1 to R4 are defined above; and when R4 represents a hydrogen atom in the obtained quinazolinedione compound(s) of the formula (4), N-alkylating a quinazolinedione ring amide of the quinazolinedione compound(s) with an N-alkylation agent(s) to form the phenylalanine derivative(s) having a quinazolinedione skeleton of formula (5):

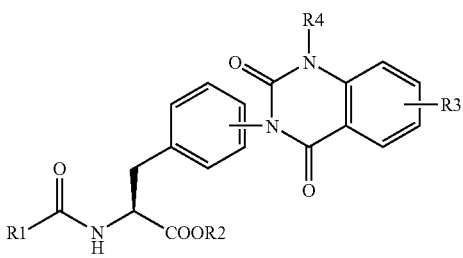

(5)

wherein R1 to R3 are defined above, R4 represents an alkyl group or a benzyl group which may have a substituent(s).

The present invention also provides the following compounds of (1) to (5), which are intermediates for production of the phenylalanine derivative(s) having a quinazolinedione ring of formula (5).

(1) Methylester of $N^{\alpha}$-(2,6-dichlorobenzoyl)-4-amino-L-phenylalanine wherein, in the formula (1), R1 represents a 2,6-dichlorophenyl group and R2 represents a methyl group, and salts thereof with chemically acceptable acids.

(2) Methylester of 5-dimethylamino-2-aminobenzoic acid wherein, in the formula (2), R3 represents a dimethylamino group, R4 represents a hydrogen atom and R5 represents a methyl group, and salts thereof with chemically acceptable acids.

(3) Methylester of 2-(3-{4-[2-(2,6-dichlorobenzoylamino)-2-methoxycarbonyl ethyl]phenyl}ureide)-5-dimethylaminobenzoic acid wherein, in the formula (3), R1 represents a 2,6-dichlorophenyl group, R2 represents a methyl group, R3 represents a dimethylamino group, R4 represents a hydrogen atom and R5 represents a methyl group, and salts thereof with chemically acceptable acids.

(4) The compound wherein, in the formula (2), R3 represents a dialkylamino group, a monoalkylamino group, an alkyl group substituted with a dialkylamino group, an alkyl group substituted with a monoalkylamino group, an alkyl group substituted with an alkynyl group, a carboxyl group, an alkoxycarbonyl group or an alkylthio group, R4 represents a hydrogen atom and R5 represents a methyl group, and salts thereof with chemically acceptable acids.

(5) The compound wherein, in the formula (3), R1 represents a 2,6-dichlorophenyl group, R2 represents a methyl group, R3 represents a dialkylamino group, a monoalkylamino group, an alkyl group substituted with a dialkylamino group, an alkyl group substituted with a monoalkylamino group, an alkyl group substituted with an alkynyl group, a carboxyl group, an alkoxycarbonyl group or an alkylthio group, R4 represents a hydrogen atom and R5 represents a methyl group, and salts thereof with chemically acceptable acids.

BEST MODE FOR CARRYING OUT THE INVENTION

The following embodiments are preferable in the present invention.

[2] The production method according to above [1], wherein, in the formulae (2) to (5), R3 represents a dialkylamino group, a monoalkylamino group, an alkyl group substituted with a dialkylamino group, an alkyl group substituted with a monoalkylamino group or an alkyl group substituted with an alkynyl group.

[3] The production method according to above [1], wherein, in the formulae (2) to (5), R3 represents a dialkylamino group, a monoalkylamino group, an amino group, a hydrogen atom, a halogen atom, an alkyl group, a perfluoroalkyl group, an alkoxy group or a nitro group.

[4] The production method according to above [1], wherein, in the formulae (2) to (5), R3 represents a dialkylamino group.

[5] The production method according to any one of above [1] to [4], wherein the carbonyl group-introducing reagent(s) is 1,1'-carbonyldiimidazole or chloroformate.

[6] The production method according to any one of above [1] to [5], wherein the base is potassium carbonate or sodium methoxide.

[7] The production method according to any one of above [1] to [6], wherein the N-alkylation agent is methyl p-toluenesulfonate.

[8] The production method according to above [1], comprising steps of reacting a carbonyl group-introducing reagent selected from the group consisting of 1,1'-carbonyldiimidazole and chloroformate and the compound of the formula (2) wherein R3 represents a dimethylamino group, R4 represents a hydrogen atom and R5 represents a methyl group with the compound of the formula (1) wherein R1 represents a 2,6-dichlorophenyl group and R2 represents a methyl group to obtain methylester of 2-(3-{4-[2-(2,6-dichlorobenzoylamino)-2-methoxycarbonylethyl]phenyl}ureide)-5-dimethylaminobenzoic acid; converting it in the presence of potassium carbonate or sodium methoxide into methylester of $N^{\alpha}$-(2,6-dichlorobenzoyl)-4-(6-dimethylamino-2,4[1H, 3H]-quinazolinedione-3-yl)-L-phenylalanine of the formula (4); and then N-alkylating the resultant with methyl p-toluenesulfonate to obtain methylester of $N^{\alpha}$-(2,6-dichlorobenzoyl)-4-(1-methyl-6-dimethylamino-2,4[1H, 3H]-quinazolinedione-3-yl)-L-phenylalanine.

[9] The production method according to above [1], comprising steps of reacting a carbonyl group-introducing reagent selected from the group consisting of 1,1'-carbonyldiimidazole and chloroformate and the compound of the formula (2) wherein R3 represents a dimethylamino group, R4 represents a methyl group and R5 represents a methyl group with the compound of the formula (1) wherein R1 represents a 2,6-dichlorophenyl group and R2 represents a methyl group to obtain the compound of the formula (3); converting it in the presence of potassium carbonate or sodium methoxide into methylester of $N^{\alpha}$-(2,6-dichloro-benzoyl)-4-(1-methyl-6-dimethylamino-2,4[1H, 3H]-quinazolinedione-3-yl)-L-phenylalanine.

Next, the compounds in the present invention are described as follows.

R1 represents a phenyl group which may have a substituent(s) or a pyridyl group which may have a substituent(s). In this connection, examples of the substituents are a halogen atom, an alkyl group, a halogenoalkyl group including a perfluoroalkyl group, an alkoxy group, a halogenoalkoxy group including a perfluoroalkoxy group, an alkylthio group, a nitro group, an alkylsulfonylamino group and a tetrazolyl group. Here, an alkyl group as a component preferably has 1 to 6 carbon atoms and particularly preferably 1 to 3 carbon atoms, and they may be same or different from each other. R1 is preferably a phenyl group substituted with a halogen atom and/or an alkyl group, and, for example, they are preferably 2,6-dichlorophenyl group, 2,6-dimethylphenyl group, 2-chloro-6-methylphenyl group, 2-chlorophenyl group, 2-methylphenyl group, 2,4,6-trichlorophenyl group, 2,4,6-trimethylphenyl group and 2,6-dichloro-4-methylphenyl group.

R2 is an alkyl group which may have a substituent(s). In this connection, an alkyl group preferably has 1 to 6 carbon atoms and particularly preferably 1 to 3 carbon atoms.

When R2 has a substituent(s), such substituent(s) include a substituted or unsubstituted lower alkylcarbonyloxy group, a substituted or unsubstituted lower alkoxycarbonyloxy group, a substituted or unsubstituted amino group, a lower alkoxy group, a halogen atom, a substituted or unsubstituted aryl group, a substituted or unsubstituted heteroaryl group and a substituted or unsubstituted carbamoyl group.

Here, when the substituent(s) of R2 is a lower alkylcarbonyloxy group, a lower alkoxycarbonyloxy group or a lower alkoxy group, alkyl and alkoxy thereof preferably have 1 to 6 carbon atoms, and include chain, cyclic, linear and branched ones.

Further, when the substituent(s) of R2 is an aryl group, it represents a mono- or bi-cyclic aromatic hydrocarbon group having 6 to 10 carbon atoms. For example, it includes a phenyl group and a naphthyl group. When the substituent(s) of R2 is a heteroaryl group, it represents a 5 to 8 membered mono-, bi- or tricyclic aromatic heterocyclic group including 1 to 4 hetero atoms selected from the group consisting of an oxygen atom, a sulfur atom and a nitrogen atom as a cyclic atom. For example, they include a pyridyl group, a pyridazinyl group, a pyrimidyl group, a pyrazinyl group, a furyl group, a thienyl group, a pyrrolyl group, an isoxazolyl group, an oxazolyl group, an isothiazolyl group, a thiazolyl group, a pyrazolyl group, an imidazolyl group, a tetrazolyl group, an indolyl group, a benzimidazolyl group, a quinolyl group and an isoquinolyl group. Here, a substituent(s) of the aryl group and the hetero aryl group is, for example, a halogen atom, an alkoxy group, an alkyl group, a hydroxy group, a halogenoalkyl group and a halogenoalkoxy group. Among these, a pyridyl group, a furyl group and a thienyl group are preferred.

Meanwhile, when the substituent(s) of R2 is a lower alkylcarbonyloxy group or a lower alkoxycarbonyloxy group, the substituent(s) thereof include a lower alkyl group, a lower alkenyl group, a lower alkoxy group, a hydroxy group, an amino group and an amino group substituted with a lower alkyl group including monosubstitution or disubstitution thereof. A methyl group and an ethyl group are preferred among these.

When the substituent(s) of R2 is an amino group, the substituent(s) thereof include a lower alkyl group, a lower alkoxycarbonyl group and a lower alkylsulfornyl group. Among these, a methyl group and an ethyl group are preferable. Here, two substituents may bond together to form a ring and, when forming a ring, they may also sandwich an oxygen, nitrogen or sulfur atom between them. For example, a substituted amino group includes a cyclic amino group such as 1-piperidinyl group and 4-morphonyl group, a cyclic amide group such as 2-oxo-1-pyrrolidinyl group and a cyclic urea group such as 2-oxoimidazoline-1-yl group and 2-oxoimidazolidine-1-yl group.

Further, when the substituent(s) of R2 is an aryl group or a heteroaryl group, the substituent(s) thereof include a halogen atom, an alkoxy group, an alkyl group, a hydroxy group, a halogenoalkyl group and a halogenoalkoxy group.

When the substituent(s) of R2 is a carbamoyl group, the substituent(s) thereof include a lower alkyl group and a phenyl group, and mono- and di-substitutions thereof are also included.

When R2 has a substituent(s), the substituent(s) thereof is preferably a lower alkylcarbonyloxy group, a chlorine atom, a pyridyl group, a furyl group, a thienyl group and a lower dialkylcarbamoyl group.

In the formula (1), an amino group is preferably in the para position among oltho, meta and para positions on a benzene ring.

R3 represents a dialkylamino group, a monoalkylamino group, an amino group, a hydrogen atom, a halogen atom, an alkyl group, a perfluoroalkyl group, an alkoxy group, a nitro group, an alkyl group substituted with a dialkylamino group, an alkyl group substituted with a monoalkylamino group, an alkyl group substituted with an amino group, an alkyl group substituted with an alkenyl group, an alkyl group substituted with an alkynyl group, a carboxyl group, an alkoxycarbonyl group, an alkylthio group or an arylthio group, and R4 represents a hydrogen atom, an alkyl group or a benzyl group which may have a substituent(s). While R5 may be whatever OR5 is removed from COOR5 by a base, an alkyl group and an alkylcarbonyl group are preferable. In R3 to R5, an alkyl group as a component preferably has 1 to 6 carbon atoms and particularly preferably 1 to 3 carbon atoms.

R3 are preferably a dialkylamino group, a hydrogen atom, a halogen atom, a monoalkylamino group, an alkyl group substituted with a dialkylamino group, an alkyl group substituted with a monoalkylamino group, an alkyl group substituted with an alkynyl group, a carboxyl group, an alkoxycarbonyl group or an alkylthio group. Particularly preferred ones are a dialkylamino group, a monoalkylamino group, an alkyl group substituted with a dialkylamino group, an alkyl group substituted with a monoalkylamino group, an alkyl group substituted with an alkynyl group, a carboxyl group, an alkoxycarbonyl group and an alkylthio group.

A dialkylamino group represents an amino group disubstituted with an alkyl group having 1 to 6 carbon atoms, including a cyclic one. Preferably it is an amino group disubstituted with an alkyl group having 1 to 3 carbon atoms or a cyclic amino group having 2 to 6 carbon atoms. For example, it includes a dimethylamino group, a diethylamino group, a methylethylamino group, a pyrrolidinyl group, a piperidyl group, a dipropylamino group, a methylpropylamino group and an ethylpropylamino group.

A monoalkylamino group represents an amino group monosubstituted with an alkyl group having 1 to 6 carbon atoms, including alkylamino group with a cyclic alkyl group(s). Preferably it is an amino group monosubstituted with an alkyl group having 1 to 4 carbon atoms such as a methylamino group, an ethylamino group, a propylamino group, an isopropylamino group, a butylamino group and a cyclopropylmethylamino group.

An alkyl group substituted with a dialkylamino group is an alkyl group having 1 to 6 carbon atoms, which is substituted with the same substituent(s) as those of the dialkylamino group. Preferably it is an alkyl group having 1 to 3 carbon atoms, which is substituted with the same substituent(s) as those of the dialkylamino group. For example, it includes either of a methyl group, an ethyl group or a propyl group substituted with a dimethylamino group, a diethylamino group, a methylethylamino group, a pyrrolidinyl group, a piperidyl group, a dipropylamino group, a methylpropylamino group or an ethylpropylamino group. Particularly preferable ones are a dimethylaminomethyl group, a diethylaminomethyl group, a methylethylaminomethyl group and the like.

An alkyl group substituted with a monoalkylamino group is an alkyl group having 1 to 6 carbon atoms, which is substituted with the same substituent(s) as those of the monoalkylamino group. Preferably it is an alkyl group having 1 to 3 carbon atoms, which is substituted with the same substituent(s) as those of the monoalkylamino group. For example, it includes either of a methyl group, an ethyl group or a propyl group substituted with a methylamino group, an ethylamino group, a propylamino group, an isopropylamino group, a butylamino group or a cyclopropylmethylamino group. Particularly preferable ones are a methylaminomethyl group, an ethylaminomethyl group, a methylaminoethyl group, an ethylaminoethyl group and the like.

An alkyl group substituted with an amino group is an alkyl group having 1 to 6 carbon atoms, which is substituted with an amino group, and preferably an alkyl group having 1 to 3 carbon atoms, which is substituted with an amino group. For example, it includes an aminomethyl group, an aminoethyl group, an aminopropyl group and the like.

An alkyl group substituted with an alkenyl group is an alkyl group having 1 to 6 carbon atoms, which is substituted with an alkenyl group having 2 to 6 carbon atoms, and preferably an alkyl group having 1 to 3 carbon atoms, which is substituted with an alkenyl group having 2 to 4 carbon atoms. For example, it includes —CH2CH=CH2, —CH2CH2CH=CH2 and the like.

An alkyl group substituted with an alkynyl group is an alkyl group having 1 to 6 carbon atoms, which is substituted with an alkynyl group having 2 to 6 carbon atoms, and preferably an alkyl group having 1 to 3 carbon atoms, which is substituted with an alkynyl group having 2 to 4 carbon atoms. For example, it includes —CH2C≡CH, —CH2CH2C≡CH and the like.

An alkoxycarbonyl group represents an alkoxycarbonyl group having 2 to 7 carbon atoms and preferably having 2 to 4 carbon atoms, such as a methoxycarbonyl group, an ethoxycarbonyl group and a propyloxycarbonyl group.

An alkylthio group represents a thio group substituted with an alkyl group having 1 to 6 carbon atoms and preferably a thio group substituted with an alkyl group having 1 to 3 carbon atoms, such as a methylthio group, an ethylthio group and a propylthio group.

An arylthio group represents a phenylthio group and a naphthylthio group.

Particularly, R3 is preferably a a dimethylamino group, a diethylamino group, a methylethylamino group, a pyrrolidinyl group, a piperidyl group, a methylamino group, an ethylamino group, a propylamino group, a cyclopropylmethylamino group, a dimethylaminomethyl group, a diethylaminomethyl group, a dimethylaminoethyl group, a diethylaminoethyl group, a methylaminomethyl group, an ethylaminomethyl group, a propylaminomethyl group, a methylaminoethyl group, an ethylaminoethyl group, a propylaminoethyl group, HC≡CCH2 group, a carboxyl group, a methoxycarbonyl group, an ethoxycarbonyl group, a methylthio group or an ethylthio group.

R4 is preferably a hydrogen atom or an alkyl group. In the formula (2), (3) and (4), a hydrogen atom is further preferable and, in the formula (5), an alkyl group is further preferable. While a substituent(s) of a benzyl group includes an alkyl group, an alkoxy group, a halogen atom and the like, an unsubstituted benzyl group is preferable.

R5 is particularly preferably an alkyl group.

In the formula (2), it is preferable that R3 is in the para position to an amino group.

The synthetic intermediates of the formula (1) are synthesized as follows.

A phenylalanine having a nitro group on an aromatic ring and acid chloride are condensed under the conditions of the well-known method, Schotten-Baumann reaction (such as N. O. V. Sonntag, Chem. Rev. 52, 272, 1953) to produce acylphenylalanine derivatives. Then, said carboxylic acid is esterified using the well known method (such as R. C. Larock Comprehensive Organic Transformations (2nd Ed.), p. 1932-1941, Wiley-VCH, New York) to synthesize alkylester of acylphenylalanine. The conventional method, catalytic reduction with a transition metal catalyst(s) (such as R. C. Larock Comprehensive Organic Transformations (2nd Ed.), p. 821-828, Wiley-VCH, New York) is applied to the synthesized substance in the presence of hydrogen gas to obtain the corresponding compounds of the formula (1).

For example, as the method for producing methylester of $N^{\alpha}$-(2,6-dichlorobenzoyl)-4-amino-L-phenylalanine which is a new synthetic intermediate wherein, in the formula (1), R1 represents a 2,6-dichlorophenyl group and R2 represents a methyl group, said compound can be synthesized by following processes: condensing a publicly-known and commercially available 4-nitro-L-phenylalanine and a similarly publicly-known and commercially available 2,6-dichlorobenzoylchloride; subjecting the resultant to methyl esterification; and reduction of a nitro group.

Concretely, 4-nitro-L-phenylalanine and 2,6-dichlorobenzoylchloride are condensed in a mixed solvent of a sodium hydroxide aqueous solution and acetone with keeping the reaction temperature at 5 to 15° C., and then crystallization is conducted to obtain a corresponding condensed substance, $N^{\alpha}$-(2,6-dichlorobenzoyl)-4-nitro-L-phenylalanine almost quantitatively.

Subsequently, the condensed substance is suspended into methanol, and methyl esterification is conducted by heating with adding concentrated sulfuric acid. Then, crystallization is conducted to obtain a corresponding methyl esterified substance, methylester of $N^{\alpha}$-(2,6-dichlorobenzoyl)-4-nitro-L-phenylalanine almost quantitatively.

Then, catalytic reduction reaction is conducted to the methyl esterified substance using a transition metal catalyst(s) of a nitro group which is a well-known method (such as F. S. Dovell et al., J. Am. Chem. Soc., 87, 2767, 1965) and preferably using a platinum carbon catalyst poisoned with sulfur, and hydrogen gas. Thereafter, crystallization is conducted to obtain methylester of $N^{\alpha}$-(2,6-dichlorobenzoyl)-4-amino-L-phenylalanine in high yield, wherein, in the formula (1), R1 represents a 2,6-dichlorophenyl group and R2 represents a methyl group.

The yield in case of going through the three steps from 4-nitro-L-phenylalanine is about 90%.

Meanwhile, the above-mentioned synthesizing method is not a sole method for producing the compound of the formula (1) and does not limit the method of the present invention. Similarly, the yield indicates an average value thereof and doe not limit the value.

On the other hand, as the method for producing the compound of the formula (2), said compound can be obtained by well-known methods from commercially available trisubstituted benzene derivatives.

For example, as the method for producing methylester of 5-dimethylamino-2-aminobenzoic acid which is a new synthetic intermediate wherein, in the formula (2), R3 represents a dimethylamino group, R4 represents a hydrogen atom and R5 represent a methyl group, said compound can be synthesized by following processes: dimethyl amination, methyl esterification and reduction of a nitro group from a publicly-known and commercially available 5-chloro-2-nitrobenzoic acid.

Concretely, 5-chloro-2-nitrobenzoic acid is dissolved in a dimethylamine aqueous solution and heated to produce 5-dimethylamino-2-nitrobenzoic acid. Hydrochloric acid is added to the reaction solution to precipitate out the product as a solid material. The solid material is separated to obtain 5-dimethylamno-2-nitrobenzoic acid almost quantitatively.

Next, the 5-dimethylamno-2-nitrobenzoic acid is dissolved in concentrated sulfuric acid/methanol and heated to conduct methyl esterification in order to produce methylester of 5-dimethylamino-2-nitrobenzoic acid, which is a well-known method. Toluene and water are added to the reaction solution, and the obtained product is extracted to an organic layer, concentrated, and crystallized to obtain 5-dimethylamino-2-nitrobenzoic acid in high yield.

Next, catalytic reduction is conducted to a nitro group of methylester of 5-dimethylamino-2-nitrobenzoic acid under the acidic condition by hydrochloric acid, using transition metal catalysts such as palladium carbon and hydrogen gas in a methanol solvent. Crystallization is conducted to obtain methylester of 5-dimethylamino-2-aminobenzoic acid/dihydrochloride in high yield.

The yield via the three processes from 5-chloro-2-nitrobenzoic acid is about 80%.

Further, thus obtained methylester of 5-dimethylamino-2-amino benzoic acid of the formula (2) can be obtained stably as salts with acidic substances, e.g., hydrochloride.

However, the above-mentioned synthesizing method is not a sole method for producing the compound of the formula (2) and does not limit the production method of the present invention. Similarly, the yield indicates an average value thereof and does not limit the value.

The step 1 of the production method of the present invention is explained below.

The method for producing phenylalanine derivatives having a quinazolinedione ring of the formula (5) in the present invention is as follows. The compound of the formula (1) which is the important intermediate and the compound of the formula (2) are converted into asymmetric urea intermediates by using a carbonyl group-introducing reagent(s), preferably 1,1'-carbonyldiimidazole or chloroformate, and then the compound of the formula (3) is converted to the compound of the formula (4) under mild basic condition.

In case of the compound wherein R4 in the formula (4) represents a hydrogen atom, the compound can be prepared without isolating the compound of the formula (4), by successively conducting N-alkylation reaction with N-alkylation agents under basic condition. It may be also possible to isolate the compound of the formula (4) and then conduct N-alkylation reaction.

For example, an amino group of methylester of $N^{\alpha}$-(2,6-dichlorobenzoyl)-4-amino-L-phenylalanine of the formula (1) is converted into carbonylimidazolyl by 1,1'-carbonyldiimidazole using an organic solvent(s) having suitable solubility such as, particularly preferably, acetonitrile. Without isolating the intermediates thereof, methylester of 5-dimethylamino-2-aminobenzoic acid of the formula (2) is put into the reaction solvent to be able to obtain methylester of 2-(3-{4-[2-(2,6-dichlorobenzoylamino)-2-methoxycarbonylethyl]phenyl}ureide)-5-dimethylaminobenzoic acid of the formula (3), which is asymmetric urea intermediates, in high yield.

In the present specification, "a carbonyl group-introducing reagent(s)" indicates those wherein only a carbonyl group in atomic groups of a quinazolinedione ring is derived from the present reagent. For instance, they include 1,1'-carbonyldiimidazole (Organic syntheses collective volume V, P. 201-204, Wiley, New York, 1973, as a synthetic example thereof), chloroformate and the like. These are publicly known and commercially available.

Further, it is also possible to use reagents wherein an imidazolyl group of 1,1'-carbonyldiimidazole is substituted with other heteroaryl removing group(s), such as 1,1'-carbonyldi(1,2,4-triazole) (an imidazolyl group in this reagent is substituted with a triazoyl group and the reagent is commercially available). The substituents thereof are not limited to only an imidazolyl group and a triazoyl group. It is also possible to use other heteroaryl removing groups as the substituents.

It is further possible to use N,N'-disuccinimidyl carbonate (DSC) (N-hydroxysuccinimide in this reagent is a removing group and the reagent is commercially available).

Chloroformate includes reagents having 2 to 10 carbon atoms, such as phenyl chloroformate, nitrophenyl chloroformate, methoxyphenyl chloroformate, methyl chloroformate, ethyl chloroformate, isobutyl chloroformate, octyl chloroformate and benzyl chloroformate, though they are not limited to these examples.

Similarly, it is also possible to use phosgene and phosgene analogues such as triphosgene as the carbonyl group-introducing reagents. These are gas or liquid and highly toxic (Reference: RTECS SY 5600000) as compared with the above reagents and therefore difficult to deal with. Further, since a particular kind of facilities is usually required and distribution thereof is limited, these reagents are not very favorable in the carbonyl group-introducing reagents.

1,1'-carbonyldiimidazole is particularly preferred as a carbonyl group-introducing reagents. When 1,1'-carbonyldiimidazole is used, it is superior in that the amount of produced by-products is small and the objective asymmetric urea intermediates are obtained in high yield.

A carbonyl group-introducing reagents is preferably used in 0.8 to 1.2 mol equivalent weight to 1 mol of the compound of the formula (1).

The compound of the formula (2) is preferably used in 0.8 to 1.2 mol equivalent weight to 1 mol of the compound of the formula (1).

The solvents of the present reaction include organic solvents having suitable solubility to the compounds of the formula (1) such as methylester of $N^\alpha$-(2,6-dichlorobenzoyl)-4-amino-L-phenylalanine. For example, it is possible to use acetonitrile, tetrahydrofuran (THF), N,N-dimethylformamide (DMF), dimethylsulfoxide (DMSO), halogenated carbon hydride such as methylene chloride, pyridine, pyrrolidone, N-methylpyrrolidone, or mixed solvents thereof.

Above all, when acetonitrile is used, products can be easily separated from the reaction solvent by filtration. Therefore, it is possible to isolate very pure asymmetric urea intermediates of the formula (3) by only a simple separation with filtration. Since it does not require any cumbersome operations such as extraction and concentration of solvents, it is useful as industrialized process. Similarly, it is also possible to obtain crystals of the objective compound by the steps of the reaction with N,N-dimethylformamide (DMF); adding poor solvents such as alcohols having 1 to 10 carbon atoms or water to precipitate asymmetric urea intermediates as a solid substance; and then separation by filtration thereof. As a result, acetonitrile and N,N-dimethylformamide are particularly preferable as the solvents of the present reaction.

The concentration of the above reaction is preferably that applicable as industrialized process. For example, when acetonitrile is used as a reaction solvent, the reaction should be conducted in 1 to 0.01M and particularly preferably around 0.2M, from the point of flowability in stirring the reaction solution or crystallizing solution.

When the compound of the formula (1) is converted into carbonylimidazolyl by carbonyl group-introducing reagents such as 1,1'-carbonyldiimidazole, the reaction temperature thereof is preferably within the range of around 0° C. to not above the boiling point of the reaction solvent. To conduct the reaction around 0° C. to not above 10° C. is more industrially preferable in that it is useful for inhibiting side reactions and improving the yield. The reaction time is preferable around 1 to 5 hours.

In the condensation reaction of the compound of the formula (1) converted into carbonylimidazolyl with methylester of 5-dimethylamino-2-aminobenzoic acid of the formula (2), the reaction temperature thereof is preferably within the range of around 0° C. to not above the boiling point of the applied solvent. Particularly, the reaction is more preferably conducted at the reaction temperature of around 50° C. since urea bond formation reaction is completed in around 2 to 3 hours and the asymmetric urea intermediates of the formula (3) can be obtained in high yield.

However, the reaction temperature and time are not limited to the above and the reaction time is determined by the balance with the reaction temperature. It is desirable from the industrial point of view that the reaction solution is controlled by analytical methods such as HPLC.

In the above reaction, input order of raw materials and reagents is not particularly limited. However, the method wherein the compound of the formula (1) is first reacted with a carbonyl group-introducing reagent(s) to convert into carbonylimidazolyl and then reacted with the compound of the formula (2) is more preferable from the point of the high yield and side reactions as compared with the method wherein the compound of the formula (2) is first converted into carbonylimidazolyl. While, in the production method of the present invention, the compound of the formula (2) may be first converted into carbonylimidazolyl, and the compound of the formula (1), a carbonyl group-introducing reagent(s) and the compound of the formula (2) may be reacted simultaneously.

Next, described herein is the step 2.

The asymmetric urea intermediates of the formula (3) form a quinazolinedione ring in the presence of a base in a suitable reaction solvent to give the quinazolinedione compounds of the formula (4).

The "base" herein includes an inorganic base and organic base. Inorganic bases include salts with alkali metals such as potassium carbonate, sodium carbonate, cesium carbonate, sodium methoxide, sodium ethoxide and the like; and salts with alkaline earth metals such as calcium carbonate and magnesium carbonate. Organic bases include triethylamine, ethanolamine, morpholine, piperidine, dicyclohexylamine, 1,8-diazabicyclo[5.4.0]undec-7-ene (DBU) and N,N-diisopropyl-N-ethylamine (DIPEA). Inorganic bases are preferable and particularly potassium carbonate and sodium methoxide are preferable.

The base is preferably used in 0.1 to 2.0 mol equivalent weight to 1 mol of the compound of the formula (3), and it is more preferable that 1 mol equivalent weight or less of a catalyst is used. The reaction time is preferably 1 to 6 hours.

For example, when potassium carbonate is used as a base, 0.1 to 2 mol equivalent weight thereof is preferable and 0.2 to 0.4 mol equivalent weight is more preferable. When sodium methoxide is used as a base, 0.1 to 1.0 mol equivalent weight thereof is preferable and 0.2 to 0.4 mol equivalent weight is more preferable. 1 to 2 hours of the reaction time are enough at that time.

The solvents in the above reactions may be those in which the compound of the formula (3) is dissolved and the reaction proceeds smoothly. For example, they include dimethylformamide (DMF) and a mixed solvent with alcohols containing dimethylformamide as a main ingredient, though the solvents are not limited to these.

Meanwhile, when potassium carbonate is used as a base, it is preferable to use a mixed solvent of DMF and methanol from the point of shortening of the reaction time. As the relative proportions of the mixed solvent of DMF and methanol, around 10 to 1 is suitable, though the proportions are not limited to this.

As the reaction concentration of the above reactions, it is preferable that the reaction is conducted in the concentration applicable as industrialized process of within 0.01 to 2M and, for example, around 0.25M in case of the mixed solvent of DMF and methanol, though the concentration thereof is not limited to these.

As the reaction temperature, 0° C. to not above the boiling point of the solvent, and preferably around 25° C. is suitable.

The quinazolinedione compounds of the formula (4) produced by the above reactions can be precipitated as solid substance by adding water or an aqueous solution of hydrochloric acid dropwise to the reaction solution, or by adding the reaction solution to water or an aqueous solution of hydrochloric acid, and then precipitated substance can be isolated by the typical separating methods.

When potassium carbonate is used as a base, the quinazolinedione ring formation reaction is conducted to the asymmetric urea intermediates of the formula (3) and then N-methylation reaction can be soon linked after that without isolating the compound of the formula (4) and, therefore, one process in the reaction processes can be skipped. When taking account of improvement in production efficiency from the point of industrialization, this method is particularly useful as industrialized process since the isolating process of the compound of the formula (4) can be simplified.

Finally, described herein is the step 3.

In the formula (4), when R4 is a hydrogen atom, the compound can be derived into quinazolinedione compounds of the formula (5) with N-alkylation agents in the presence of a base.

Meanwhile, it is also possible to isolate the quinazolinedione compounds of the formula (4), which is produced in the step 2, and then N-alkylate. However, it is preferable from the point of industrialization to N-alkylate without isolation.

In the present specification, "N-alkylation agents" indicate reagents which can introduce an alkyl group on a nitrogen atom, and haloalkane, alkyl sulfonate and benzyl halide which may be substituted are included, for example.

Here, haloalkane and alkyl sulfonate are preferably those having 1 to 10 carbon atoms. Those having 1 to 6 carbon atoms are further preferable and those having 1 to 3 carton atoms are particularly preferable. Haloalkane includes, for example, methyl iodide and ethyl iodide, and alkyl sulfonate includes, for example, methyl methanesulphonate, ethyl methanesulphonate, methyl ethanesulphonate, ethyl ethanesulphonate, methyl p-toluenesulphonate and ethyl p-toluenesulphonate. Benzyl halide includes benzylchloride, benzylbromide and the like, and the substituents thereof are an alkyl group, an alkoxy group, a halogen atom and the like.

For example, in the production of the compound wherein R4 in the formula (5) is a methyl group, methyl p-toluenesulphonate is suitable from the point of industrialization. Namely, methyl p-toluenesulphonate has the higher boiling point as compared with methyl iodide and is easy to deal with under room temperature. Further, methyl p-toluenesulphonate has the favorable flowability of the reaction solution and is suitable for the industrialized process with solution sending.

As the usage amount of N-alkylation agents, the range of 1 to 10 mol equivalent weight thereof and preferably around 1.2 to 2.0 mol equivalent weight is suitable to the compound of the formula (3) or (4). The amount of the reagents can be increased or decreased in accordance with progress of the reaction.

A base includes inorganic bases and organic bases. Here, examples of inorganic bases are salts with alkali metals such as potassium carbonate, sodium carbonate, cesium carbonate, sodium methoxide, sodium ethoxide and the like; and salts with alkaline earth metals such as calcium carbonate and magnesium carbonate. Organic bases include triethylamine, ethanolamine, morpholine, piperidine, dicyclohexylamine, 1,8-diazabicyclo[5.4.0]undec-7-ene (DBU) and N,N-diisopropyl-N-ethylamine (DIPEA). Inorganic bases are preferable and particularly potassium carbonate is preferable.

The base is preferably used in 1.5 to 2 mol equivalent weight to the compound of the formula (3) or (4) and more preferably around 1.8 mol equivalent weight, while the amount is not limited to these and can be increased or decreased in accordance with progress of the reaction.

The reaction solvents may be those in which the compound of the formula (3) or (4) is dissolved and the reaction proceeds smoothly. For example, they include dimethylformamide (DMF) and a mixed solvent with alcohols containing dimethylformamide as a main ingredient, though the solvents are not limited to these. Meanwhile, when potassium carbonate is used as a base, it is preferable to use a mixed solvent of DMF and methanol from the point of shortening of the reaction time. As the relative proportions of the mixed solvent of DMF and methanol, around 10 to 1 is suitable, though the proportions are not limited to this. As the reaction concentration of the above reactions, it is preferable that the reaction is conducted in the concentration applicable as industrialized process of within 0.01 to 2M and, for example, around 0.25M in case of the mixed solvent of DMF and methanol, though the concentration thereof is not limited to these.

As the reaction temperature, 0° C. to not above the boiling point of the reaction solvent, and preferably around 40° C. is suitable, though the temperature thereof is not limited to these. The reaction time may be 3 to 18 hours, and it is desirable from the industrial point of view that the reaction solution is administered by analytical methods such as HPLC.

For example, an asymmetric urea intermediate wherein, in the formula (4), R1 is 2,6-dihlorophenyl group, R2 is a methyl group and R3 is a dimethylamino group is dissolved at 25° C. in a mixed solvent of DMF and methanol. The quinazolinedione ring formation reaction is conducted by stirring for 2 hours using 0.2 mol equivalent weight of potassium carbonate to the compound of the formula (4). Then, 1.5 mol equivalent weight of methyl p-toluenesulphonate and 1.8 mol equivalent weight of potassium carbonate are added to conduct N-methylation reaction. Two processes are gone through from the formula (4) to be able to obtain methylester of $N^\alpha$-(2,6-dichlorobenzoyl)-4-(1-methyl-6-dimethylamino-2,4 [1H,3H]-quinazolinedione-3-yl)-L-phenylalanine of the formula (5) in the yield of 80 to 90%.

The compound of the formula (5) can be precipitated as solid substance by adding water to the reaction solvent and isolated by the typical separating methods such as filtration, though the method is not limited to this.

The above production methods describe the case using the compound wherein, in the formula (2), R4 is a hydrogen atom. As for the compounds wherein, in the formula (2), R4 is an alkyl group or a benzyl group which may have a substituent(s), as the reaction process with N-alkylation agents is not necessary, the compound of the formula (1) and the compound of the formula (2) are derived into asymmetric urea intermediates of the formula (3) by using a carbonyl group-introducing reagent(s) and preferably 1,1'-carbonyldiimidazole; the compound of the formula (3) is converted to the compound of the formula (4) under mild basic condition; and then the compound of the formula (4) is isolated to obtain the objective compound of the formula (5) (because the formula (4) and the formula (5) are identical in this case).

From the above production methods, herein provided is the industrially applicable method for producing phenylalanine derivatives having a quinazolinedione ring of the formula (5) via the crucial intermediate (3) from crucial intermediates of the formulae (1) and (2).

Meanwhile, when R3 is a monoalkylamino group, an amino group, an alkyl group substituted with a monoalkylamino group or an alkyl group substituted with an amino group, a hydrogen atom(s) directly bonding to a nitrogen atom constituting the amino group may be protected in advance by a proper protecting group(s) and then the protection thereof may be removed by suitable methods of removal of protection. The methods for protection and removal of protection are described in, for example, "Protecting group in organic synthesis" by Theodora W. Greene, Peter G. M. Wuts, Second edition, John Wiley & Sons Inc., New York, 1991, 309-385.

For example, a hydrogen atom(s) directly bonding to a nitrogen atom constituting the amino group may be substituted, by using acylation agents in ordinary acylation methods, with an alkylcarbonyl group having 2 to 7 carbon atoms which may have a substituent(s) such as an acetyl group, a propionyl group, a butyryl group, an isobutyryl group, a valeryl group, an isovaleryl group, a pivaloyl group, a trifluoroacetyl group and the like; an arylcarbonyl group which may have a substituent(s) such as a benzoyl group; an arylalkylcarbonyl group which may have a substituent(s) such as a benzylcarbonyl group; an alkoxycarbonyl group having 2 to 7 carbon atoms which may have a substituent(s) such as a methoxycarbonyl group, an ethoxycarbonyl group, a propyloxycarbonyl group, a butoxycarbonyl group, a tertiary-butoxycarbonyl group, a trifluoromethoxy carbonyl group and the like; an aryloxycarbonyl group which may have a substituent(s) such as a phenoxycarbonyl group; and an arylalkyloxycarbonyl group which may have a substituent(s) such as a benzyloxycarbonyl group.

In this case, after completion of the reaction of the first, second or third step in the present invention, particularly after the completion of the N-alkylation reaction in the third step of the present invention, a protecting group(s) can be removed under the acidic condition or the basic condition and the like in case of an alkylcarbonyl group having 2 to 7 carbon atoms which may have a substituent(s), an arylcarbonyl group which may have a substituent(s) and an arylalkylcarbonyl group which may have a substituent(s); under the basic condition and the like in case of an alkoxycarbonyl group having 2 to 7 carbon atoms which may have a substituent(s) and an aryloxycarbonyl group which may have a substituent(s); under the acidic condition and the like in case of a tertiary-butoxycarbonyl group; and under the catalytic reduction condition (hydrogenating reaction) and the like.

Further, for instance, a hydrogen atom(s) directly bonding to a nitrogen atom constituting the amino group may be substituted, by using benzylation reagents in ordinary benzylation methods, with an arylalkyl group which may have a substituent(s) such as a benzyl group, a phenethyl group, a methylbenzyl group, a methoxybenzyl group and a halobenzyl group, and the like. In this case, after completion of the reaction of the first, second or third step in the present invention, particularly after the completion of the N-alkylation reaction in the third step of the present invention, a protecting group(s) can be removed under the catalytic reduction condition (hydrogenating reaction) and the like.

Meanwhile, the substituents in case of the above protecting groups "which may have a substituent(s)" include, for example, a halogen atom, an alkoxy group, an alkyl group, a hydroxy group, a halogenoalkyl group and a halogenoalkoxy group.

The "halogen atom" in the present specification indicates a fluorine atom, a chlorine atom, a bromine atom and an iodine atom. The "halogeno-" as the component in a substituent indicates fluoro-, chloro-, bromo- and iodo-.

The "chemically acceptable acids" in the formula (1) or (2) include inorganic acids such as hydrochloric acid, sulfuric acid, phosphoric acid, nitric acid and hydrobromic acid; organic carboxylic acid such as acetic acid, citric acid, benzoic acid, maleic acid, fumaric acid, tartaric acid, succinic acid, trifluoroacetic acid, tannic acid, butyric acid, hibenzic acid, pamoic acid, enanthic acid, decanoic acid, teoclic acid, salicylic acid, lactic acid, oxalic acid, mandelic acid and malic acid; and organic sulfonic acid such as methanesulfonic acid, p-toluenesulfonic acid and benzenesulfonic acid. The free forms are particularly preferable in the compound of the formula (1) and the hydrochloride is particularly preferable in the compound of the formula (2). They may be hydrates or solvates thereof.

In the present invention, when R3 in the formula (5) is a dialkylamino group, the resulting compound is therapeutically superior, and therefore, R3 in the formulae (2) and (3) are preferably dialkylamino groups. Among dialkylamino groups, a dimethylamino group, a diethylamino group, a methylethylamino group, a pyrrolidinyl group and a piperidinyl group are preferable. Particularly, it is preferable that R3 is a dimethylamino group.

Similarly, it is also preferable that R3 in the formulae (2) and (3) are a monoalkylamino group, an alkyl group substituted with a dialkylamino group, an alkyl group substituted with a monoalkylamino group, an alkyl group substituted with an alkynyl group, a carboxyl group, an alkoxycarbonyl group or an alkylthio group. Particularly preferred ones are a methylamino group, an ethylamino group, a propylamino group, a cyclopropylmethylamino group, a dimethylaminometyl group, a diethylaminomethyl group, a dimethylaminoethyl group, a diethylaminoethyl group, a methylaminomethyl group, an ethylaminomethyl group, a propylaminomethyl group, methylaminoethyl group, ethylaminoethyl group, a propylaminoethyl group, HC≡CCH2 group, a carboxyl group, a methoxycarbonyl group, an ethoxycarbonyl group, a methylthio group and an ethylthio group.

Among these, when R3 in the formulae (2) and (3) are a monoalkylamino group or an alkyl group substituted with a monoalkylamino group, a hydrogen atom(s) directly bonding to a nitrogen atom constituting the amino group may be substituted with an alkylcarbonyl group having 2 to 7 carbon atoms which may have a substituent(s) such as an acetyl group, a propionyl group, a butyryl group, an isobutyryl group, a valeryl group, an isovaleryl group, a pivaloyl group, a trifluoroacetyl group and the like; an arylcarbonyl group which may have a substituent(s) such as a benzoyl group; an arylalkylcarbonyl group which may have a substituent(s) such as a benzylcarbonyl group; an alkoxycarbonyl group having 2 to 7 carbon atoms which may have a substituent(s) such as a methoxycarbonyl group, an ethoxycarbonyl group, a propyloxycarbonyl group, a butoxycarbonyl group, a tertiary-butoxycarbonyl group, a trifluoromethoxy carbonyl group and the like; an aryloxycarbonyl group which may have a substituent(s) such as a phenoxycarbonyl group; and an arylalkyloxycarbonyl group which may have a substituent(s) such as a benzyloxycarbonyl group. A hydrogen atom(s) directly bonding to a nitrogen atom constituting the amino group may be substituted with an arylalkyl group which may have a substituent(s) such as a benzyl group, a phenethyl group, a methylbenzyl group, a methoxybenzyl group and a halobenzyl group, and the like. The substituents in case of the above protecting groups "which may have a substituent(s)" include a halogen atom, an alkoxy group, an alkyl group, a hydroxy group, a halogenoalkyl group and a halogenoalkoxy group.

EXAMPLES

Next, Examples will further illustrate the present invention in detail. The following Examples only explain the present invention and do not particularly limit the invention.

<Analysis Conditions>

TMS was used as an internal reference material in $^1$H and $^{13}$C NMR, and measurement was conducted with AVANCE 400 mHz NMR of Bruker BioSpin GmbH. As DMSO-$d_6$, the product (containing 0.03% TMS) of Eurisotop CEA Group was used. As an HPLC apparatus, LC10 series (Pump: LC-10AT, Controller: SCL-10A and Detector: SPD-10Avp) of Shimadzu Corporation was used. As an autosampler, KMT-100X of Kyowaseimitsu Corporation (was used (the injection volume is 10 μl as long as it is not particularly described). As an column oven, U-620 of Sugai Chemical Industry Co., LTD was used. As a chromato waveform processing, C-R7A of Shimadzu Corporation was used. As raw materials and reagents in the present Examples, commercial items thereof are used themselves without purification.

| <HPLC Analysis Conditions> | | |
|---|---|---|
| Compositions of eluting solvents: | Solution A | 0.1% TFA aqueous solution |
| | Solution B | acetonitrile containing 0.1% TFA |
| Flow volume: | | 1.0 mL/min. |
| Detector: | | UV, 254 nm |
| Used column | | reverse-phase ODS silica gel column (ODS-2 of GL Sciences, Inc.) |
| Column size: | | inner diameter of φ 4.6 mm and length of 150 mm |
| Column temperature: | | 40° C. |
| Gradient analysis condition: | | (Solution A/Solution B) = beginning (90/10) – 25 minutes later (10/90) – 30 minutes later (10/90) |
| Sample injection volume: | | 10 μl |

Synthetic Reference Example of Synthetic Intermediate (1)

Synthetic Example of the Compound (6)

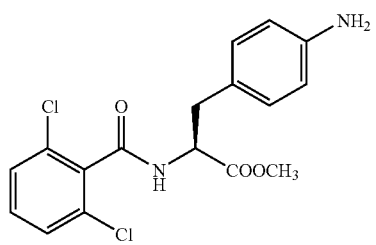

(6)

Synthesis of methylester of $N^\alpha$-(2,6-dichlorobenzoyl)-4-amino-L-phenylalanine 200 mL of water and 91 mL of acetone were mixed and 72.4 g (344 mmol) of 4-nitro-L-phenylalanine was added thereto and cooled down to 10° C. or lower. 68 mL of 6M sodium hydroxide aqueous solution was added dropwise to the solution so that the temperature thereof did not exceed 15° C. Keeping around pH 14, 73.58 g (344 mmol) of 2,6-dichlorobenzoyl chloride was slowly added dropwise thereto. In order to keep around pH 14, if needed, a sodium hydroxide aqueous solution was added dropwise. 2 hours later of completion of drop, 86 mL of 6M hydrochloric acid was added with keeping the temperature of the reaction solution at 15° C. or lower to precipitate white crystals. After maturing at 10° C. or lower, the crystals were separated, dried under reduced pressure at 60° C. to obtain 128.5 g of $N^\alpha$-(2,6-dichlorobenzoyl)-4-nitro-L-phenylalanine. (Yield: 97%) $^1$H NMR (400 MHz, DMSO-$d_6$): 9.12 (d, 1H, J=8.42 Hz), 8.16 (d, 2H, J=8.78 Hz), 7.59 (d, J=8.77Hz), 7.42 (m, 3H), 3.29 (m), 3.07 (dd, 1H, J=3.64 and 10.42 Hz). $^{13}$C NMR (100 MHz, DMSO-$d_6$): 172.25, 163.74, 146.68, 146.18, 131.51, 131.37, 131.05, 128.37, 123.55, 53.17, 36.74.

MS (FAB): m/z 383.1 (M+H)$^+$

HRMS (FAB): m/z 383.0219 (M+H)$^+$

Next, 117.3 g (306 mmol) of $N^\alpha$-(2,6-dichlorobenzoyl)-4-nitro-L-phenylalanine was added to 592 mL of methanol and dissolved. 31.6 g of 95% concentrated sulfuric acid was added dropwise being careful of heating. After the drop, the reaction was conducted for 3 hours at the reaction temperature of 40° C. After confirming completion of the reaction with HPLC, the reaction solution was cooled down to 30° C. or lower. 395 mL of water cooled down to around 10° C. in advance was added dropwise in 1 hour so that the temperature of the reaction solution did not exceed 30° C. After crystallizing out, the reaction solution was matured for 5 hours with keeping a crystallizing solution at 10° C. or lower. The crystals were separated by filtration, and then dried under reduced pressure at 60° C. to obtain 117.8 g of methylester of $N^\alpha$-(2,6-dichlorobenzoyl)-4-nitro-L-phenylalanine. (yield 97%)

$^1$H NMR (400 MHz, DMSO-$d_6$): 9.23 (d, 1H, J=8.2 Hz), 8.18 (d, 2H, J=8.8 Hz), 7.59 (d, 2H, J=8.8 Hz), 7.38-7.46 (m, 3H), 4.88 (ddd, 1H, J=6.4, 8.2 and 11 Hz), 3.69 (s, 3H), 3.31 (dd, 1H, J=6.4 and 14 Hz), 3.10 (dd, 1H, J=11 and 14 Hz).

$^{13}$C NMR (100 MHz, DMSO-$d_6$): 171.27, 163.83, 146.74, 145.80, 136.15, 131.49, 131.05, 128.42, 123.58, 53.07, 52.40, 36.39.

MS (FAB): m/z 397.2 (M+H)$^+$

HRMS (FAB): m/z 397.0345 (M+H)$^+$

Further, 115.94 g (290 mmol) of methylester of $N^\alpha$-(2,6-dichlorobenzoyl)-4-nitro-L-phenylalanine and 28.37 g (0.5 mol % to substrate) of 3% platinum carbon powder (wet) were suspended to 825 mL of methanol. Nitro groups in the suspended solution were reduced under hydrogen gas atmosphere at 30° C. for 5 hours. After confirming completion of the reaction with HPLC, the platinum catalyst was filtered out and the concentration of the reaction solution was adjusted. 539 mL of water was added dropwise thereto at the liquid temperature of around 30° C., and crystallization by cooling was conducted at 10° C. or lower. The crystals were filtered out and dried under reduced pressure at 60° C. to obtain 84.61 g of methylester of $N^\alpha$-(2,6-dichlorobenzoyl)-4-amino-L-phenylalanine. (yield 80%)

$^1$H NMR (400 MHz, DMSO-$d_6$): 9.23 (d, 1H, J=7.8 Hz), 7.38-7.47 (m, 3H), 6.90 (d, 2H, J=7.0 Hz), 6.47 (d, 2H, J=7.0 Hz), 4.57 (ddd, 1H, J=5.8, 7.8 and 9.1 Hz), 3.62 (s, 3H), 2.90 (dd, 1H, J=5.8 and 14 Hz), 2.79 (dd, 1H, J=9.1 and 14 Hz).

$^{13}$C NMR (100 MHz, DMSO-$d_6$): 171.87, 163.88, 147.52, 136.43, 131.65, 131.34, 129.90, 128.34, 124.01, 114.14, 54.57, 52.07, 36.40.

MS (FAB): m/z 367.2 (M+H)$^+$

HRMS (FAB): m/z 367.0585 (M+H)$^+$

Synthetic Reference Example of Synthetic Intermediate (2)

Synthetic Example of the Compound of Formula (7)

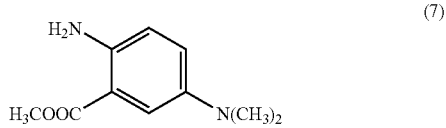

Synthesis of methylester of 2-amino-5-(dimethylamino) benzoic acid/dihydrochloride 30.0 g (148 mmol) of 5-chloro-2-nitrobenzoic acid was dissolved by stirring in 78 mL (744 mmol) of 50% dimethylamine aqueous solution under cooling in the ice bath. After the solution was put into a pressure-resistant container and sealed, the solution was stirred by heating in the oil bath for 23 hours at 60° C. The reaction solution was sufficiently cooled down and the inner pressure thereof was released. After confirming completion of the reaction by HPLC analysis, the reaction solution was put into another container (using 50 mL of water), 49.6 mL of concentrated hydrochloric acid, and then 200 mL of water were added thereto. Yellow crystals were precipitated by addition of hydrochloric acid. The crystallizing solution was matured at 10° C. overnight, separated by filtration and dried under reduced pressure to obtain 30.95 g of 5-dimethylamino-2-nitrobenzoic acid. (yield 99%)

$^1$H NMR (400 MHz, DMSO-d$_6$): 8.88 (bs, 1H), 7.97 (d, 1H, J=9.4 Hz, aryl coupling=1.76 Hz), 6.78 (d, 1H, J=9.4 Hz, aryl coupling=2.84 and 1.92 Hz), 6.71 (s, 1H, aryl coupling=2.88 and 1.60 Hz), 3.08 (s, 6H).

$^{13}$C NMR (100 MHz, DMSO-d$_6$): 168.58, 153.86, 133.94, 132.85, 127.03, 111.44, 109.69, 40.24.

MS(ESI): m/z 211.17 (M+H)$^+$, 209.27 (M−H)$^−$

Next, 40.0 g (190.30 mmol) of 5-dimethylamino-2-nitrobenzoic acid was suspended in 160 mL of methanol at 25° C. This suspension was under cooled down in the ice bath and 53.6 mL of concentrated sulfuric acid was added thereto. After adding the concentrated sulfuric acid, the temperature of the solution rose up to about 30° C. The solution was directly soaked in the bath of 60° C. and stirred by heating for 20 hours. The progress of the reaction was confirmed by HPLC, and after confirming disappearance of a raw material, 400 mL of toluene was added thereto to dilute. Then, 200 mL of water and an aqueous solution of sodium hydroxide (wherein 38.06 g of sodium hydroxide was dissolved in 200 mL of water) were added thereto. The aqueous layer was extracted with 200 mL of toluene and a toluene solvent(s) was mixed together. The toluene layer was washed with 300 mL of saturated sodium bicarbonate water. The toluene layer was further concentrated under reduced pressure (bath temperature: 50° C.) and adjusted so that the objective substance becomes about 20 wt %. After distilling under reduced pressure, crystals of the objective substance precipitated. After maturing them at room temperature for about one hour, 220 mL of n-heptane was added and further stirred at 5° C. overnight. The crystals were separated by suction filtration and washed with 100 mL of n-heptane. These wet crystals were dried under reduced pressure for 3 hours at 65° C. to obtain 34.82 g of methylseter of 5-dimethylamino-2-nitrobenzoic acid as yellow crystallized powder. (yield 82%)

$^1$H NMR (400 MHz, DMSO-d$_6$): 8.02 (d, 1H, J=9.4 Hz), 6.82 (d, 1H, J=9.36 Hz, aryl coupling=2.56 Hz), 6.78 (s, 1H, aryl coupling=2.4 Hz), 3.83 (s, 3H), 3.10 (s, 6H).

$^{13}$C NMR (100 MHz, DMSO-d$_6$): 167.70, 153.92, 132.71, 132.34, 127.24, 111.87, 110.07, 53.21, 40.28.

MS (FAB): m/z 224.24 (M)$^+$

HR MS (FAB): m/z 224.0830 (M)$^+$

Further, 10.06 g (44.9 mmol) of methylester of 5-dimethylamino-2-nitrobenzoic acid was added to 50 mL of methanol and suspended. 9.0 mL of 10M hydrochloric acid and 1.96 g (wet, 1 mol % to substrate) of 5% palladium carbon were added thereto. The reaction container was substituted with hydrogen gas and stirred at room temperature overnight. A palladium catalyst was filtered out with Celite and the filtrate was concentrated under reduced pressure by about a half amount thereof. Then, 80 mL of acetone was added to the solution and concentrated under reduced pressure three times to precipitate the compound of the formula (12). The compound was further matured at 10° C. or lower and dried under reduced pressure to 11.16 g of methylester of 2-amino-5-(dimethylamino) benzoic acid/dihydrochloride. (yield 93%)

$^1$H NMR (400 MHz, DMSO-d$_6$): 8.09 (s, 1H), 7.72 (d, 1H, J=9.0 Hz), 6.96 (d, 1H, 9.08 Hz), 5.50 (bs), 3.83 (s, 3H), 3.04 (s, 6H).

$^{13}$C NMR (100 MHz, DMSO-d$_6$): 167.12, 131.64, 126.66, 123.29, 118.7, 108.88, 52.18, 45.84.

MS (FAB): m/z 195.3 (M+H)$^+$

HR MS (FAB): m/z 195.1122 (M+H)$^+$

Example 1

Process 1

Synthetic Example of the Compound (8)

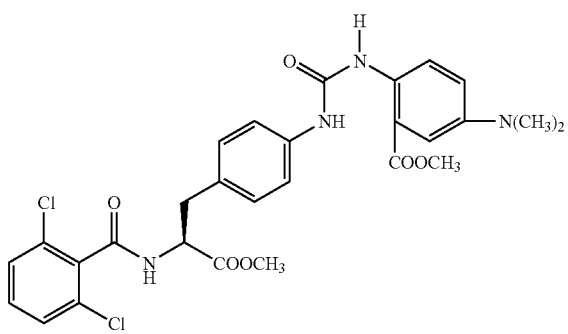

Synthesis of methylester of 2-(3-{4-[2-(2,6-dichlorobenzoylamino)-2-methoxycarbonylethyl]phenyl}ureide)-5-dimethylaminobenzoic acid Method 1: In Case of Using 1,1'-Carbonyldiimidazole (CDI) as a Carbonyl Group-Introducing Reagent 9.73 g (59.41 mmol) of 1,1'-carbonyldiimidazole was added to 310 mL of acetonitrile and dissolved. The solution was cooled down to 10° C. or lower and 20.78 g (56.58 mmol) of methylester of N$^α$-(2,6-dichlorobenzoyl)-4-amino-L-phenylalanine of the formula (6) was added thereto and stirred. 2 hours later, 15.06 g (54.50 mmol) of methylester of 2-amino-5-(dimethylamino) benzoic acid/dihydrochloride of the formula (7) was added, heated up to 50° C. and stirred for 2 hours. After completion of the reaction, 62 mL of methanol was added to the reaction solution, and the solution was cooled down to 10° C. or lower. After maturing 10 hours or more, the crystals were separated by filtration and dried under reduced pressure to obtain 30.03 g of objective methylester of 2-(3-{4-[2-(2,6-dichlorobenzoylamino)-2-methoxycarbonylethyl]phenyl}ureide)-5-dimethylaminobenzoic acid of formula (8). (yield 88%)

$^1$H NMR (400 MHz, DMSO-d6): δ 9.56 (s, 1H), 9.46 (s, 1H), 9.22 (d, 1H, J=8.0 Hz), 8.07 (d, 1H, J=9.24 Hz), 7.47-7.38 (m, 5H), 7.19 (m, 3H), 7.06 (m, 1H), 4.69 (m, 1H), 3.88 (s, 3H), 3.66 (s, 3H), 3.06 (dd, 1H, J=14.1 and 5.3 Hz), 2.93-2.88 (m, 1H), 2.88 (s, 6H)

$^{13}$C NMR (100 MHz, DMSO-d6): δ 171.72, 168.20, 163.88, 152.87, 145.63, 138.89, 136.38, 131.80, 131.64, 131.37, 130.46, 129.78, 128.36, 122.83, 119.31, 118.54, 117.18, 112.99, 54.09, 52.59, 52.18, 40.80, 36.34.

MS (FAB): m/z 586.3 (M)$^+$

HR MS (FAB): 586.1407 (M)$^+$

Method 2: In Case of Using Phenyl Chloroformate as a Carbonyl Group-Introducing Reagent 2.08 g (5.45 mmol) of methylester of N$^α$-(2,6-dichlorobenzoyl)-4-amino-L-phenylalanine of the formula (6) was added to 30 mL of acetonitrile and stirred at room temperature and dissolved. After under cooling in the ice bath, 0.83 mL of triethylamine and 0.72 mL (5.72 mmol) of phenyl chloroformate were added thereto. After warming the reaction solution to room temperature and stirring for 1.5 hours, 1.46 g (5.45 mmol) of methylester of 2-amino-5-dimethylamino benzoic acid/dihydrochloride and 1.51 mL of triethylamine were added thereto and stirred at room temperature for 3 days. Precipitated crystals were filtered out, washed with methanol and dried under reduced pressure to obtain 2.55 g of a crystalline solid substance containing objective methylester of 2-(3-{4-[2-(2,6-dichlorobenzoylamino)-2-methoxycarbonylethyl]phenyl}ureide)-5-dimethylaminobenzoic acid of formula (8). (content 61.3 wt %, yield 49%)

Meanwhile, analytical data of the compound conformed to those of the above mentioned Method 1.

Method 3: In Case of Using N,N'-Disuccinimidyl Carbonate (DSC) as a Carbonyl Group-Introducing Reagent 1.32 g (3.60 mmol) of methylester of N$^α$-(2,6-dichlorobenzoyl)-4-amino-L-phenylalanine of the formula (6) was added to 15 mL of acetonitrile and stirred at room temperature and dissolved. 1.0 g (3.90 mmol) of N,N'-disuccinimidyl carbonate (DSC) was added to the solution and stirred at room temperature. 0.98 g (3.68 mmol) of methylester of 2-amino-5-dimethylamino benzoic acid/dihydrochloride and 1.92 g of N,N-diisopropyl-N-ethylamine (DIPEA) were added to the reaction solution and stirred at 50° C. for 2.5 hours. The objective substance precipitated as a solid material as the reaction proceeded, and the suspension was cooled down to 10° C. or lower. The crystals were filtered out, washed with methanol and dried under reduced pressure to obtain 1.16 g of objective methylester of 2-(3-{4-[2-(2,6-dichlorobenzoylamino)-2-methoxycarbonylethyl]phenyl}ureide)-5-dimethylaminobenzoic acid of formula (8). (yield 55%) Meanwhile, analytical data of the compound conformed to those of the above mentioned Method 1.

Process 2

Synthetic Example of the Compound of Formula (9)

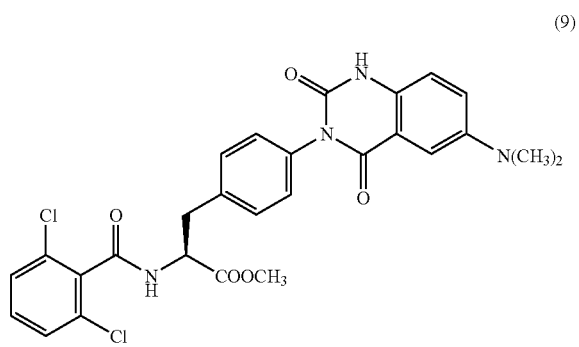

(9)

Synthesis of methylester of N$^α$-(2,6-dichlorobenzoyl)-4-(6-dimethylamino-2,4[1H,3H]-quinazolinedione-3-yl)-L-phenylalanine 40.0 g (68.14 mmol) of methylester of 2-(3-{4-[2-(2,6-dichlorobenzoylamino)-2-methoxycarbonylethyl]phenyl}ureide)-5-dimethylaminobenzoic acid of the formula (8) was added to 200 mL of N,N-dimethylformamide and stirred and dissolved at 25° C. 5.4 mL of 28% sodium methoxide/methanol solution was added thereto and stirred at 25° C. for 2 hours. After completion of the reaction, the reaction solution was added dropwise to 210 mL of an aqueous solution of hydrochloric acid to precipitate the compound of formula (14). The compound was separated and dried under reduced pressure to obtain 36.74 g of the title compound. (yield 97.2%)

$^1$H NMR (400 MHz, DMSO-d$_6$): δ 11.20 (bs, 1H), 9.29 (d, 1H, J=8.12 Hz), 7.47-7.38 (m, 5H), 7.29-7.26 (m, 1H), 7.18 (d, 2H, J=8.3 Hz), 7.12 (m, 2H), 4.81 (m, 1H), 3.69 (s, 3H), 3.22 (dd, 1H, J=14.1 and 4.8 Hz), 3.02 (dd, 1H, J=14.0 and 3.8 Hz), 2.91 (s, 6H).

$^{13}$C NMR (100 MHz, DMSO-d$_6$): δ 171.70, 163.99, 162.75, 150.18, 146.80, 137.15, 136.34, 134.80, 131.78, 131.36, 131.15, 129.84, 129.18, 128.32, 122.05, 116.48, 115.03, 108.50, 53.70, 52.29, 40.93, 36.36.

MS (FAB): m/z 555.2 (M+H)$^+$

HR MS (FAB): m/z 555.1172 (M+H)$^+$

Process 3

Synthetic Example of the Compound of Formula (10)

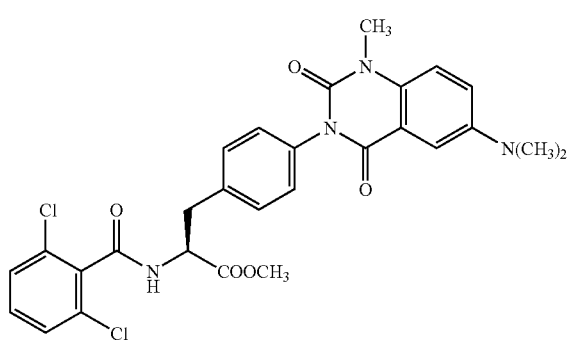

(10)

(Method 1) Synthesis of methylester of N$^\alpha$-(2,6-dichlorobenzoyl)-4-(1-methyl-6-dimethylamino-2,4[1H,3H]-quinazolinedione-3-yl)-L-phenylalanine by N-methylation of the formula (9) [A production method in case of isolating the compound of the formula (9)]

30.0 g (54.0 mmol) of methylester of N$^\alpha$-(2,6-dichlorobenzoyl)-4-(6-dimethylamino-2,4[1H,3H]-quinazolinedione-3-yl)-L-phenylalanine of the formula (9) was added to a solution containing 180 mL of N,N-dimethylformamide (DMF) and 20 mL of methanol and stirred and dissolved at 25° C. A DMF solution (20 mL as DMF) containing 15.3 g (81.1 mmol) of methyl of p-toluenesulfonic acid and 15.0 g (108.1 mmol) of potassium carbonate were added thereto. After addition thereof, the reaction solution was stirred at the reaction temperature of 40° C. for 6 hours. Then, the solution was added dropwise being careful of exothermic heating to an aqueous solution of hydrochloric acid (1.8 mL of 6M hydrochloric acid and 250 mL of water) which was cooled down in advance at 10° C. or lower. The precipitated substance was filtered out and dried at 60° C. under reduced pressure to obtain 25.3 g of the title compound of the formula (10). (yield 82%)

(Method 2) Synthesis of methylester of N$^\alpha$-(2,6-dichlorobenzoyl)-4-(1-methyl-6-dimethylamino-2,4[1H,3H]-quinazolinedione-3-yl)-L-phenylalanine [A production method in case of not isolating the compound of the formula (9)]

20 g (34.07 mmol) of methylester of 2-(3-{4-[2-(2,6-dichlorobenzoylamino)-2-methoxycarbonylethyl]phenyl}ureide)-5-dimethylaminobenzoic acid of the formula (8) was stirred and dissolved in 110 mL of N,N-dimethylformamide (DMF) at 20° C. 11 mL of methanol and 0.94 g (6.81 mmol) of potassium carbonate were added thereto and stirred at 25° C. for 1 hour. After confirming completion of the quinazolinedione ring formation reaction with HPLC, without isolating the compound of the formula (9), a DMF solution (14 mL of DMF) containing 7.74 mL (51.11 mmol) of methyl of p-toluenesulfonic acid and 8.46 g (61.33 mmol) of potassium carbonate were added to the reaction solution. N-methylation reaction was conducted to the solution at 40° C. After completion of the reaction, the reaction solution was added to water to precipitate the title compound of the formula (10) as a solid substance. The precipitated substance was filtered out and dried under reduced pressure to obtain 16.71 g thereof. (yield 86.2%)

$^1$H NMR (400 MHz, DMSO-d$_6$): δ 9.29 (d, 1H, J=8.12 Hz), 7.47-7.36 (m, 6H), 7.32-7.29 (m, 1H), 7.24 (d, 1H, J=2.84 Hz), 7.18 (d, 2H, J=8.28 Hz), 4.82 (m, 1H), 3.69 (s, 3H), 3.49 (s, 3H), 3.23 (dd, 1H, J=14.1 and 4.6 Hz), 3.02 (dd, 1H, J=13.9 and 3.5 Hz), 2.94 (s, 6H).

$^{13}$C NMR (100 MHz, DMSO-d$_6$): δ 171.73, 163.99, 161.88, 150.37, 146.73, 137.20, 136.34, 135.34, 132.06, 131.78, 131.36, 129.89, 128.99, 128.32, 121.34, 116.21, 116.00, 109.15, 53.65, 52.29, 40.75, 36.35, 30.88.

MS (ESI): m/z 569.33 (M+H)$^+$

Anal. Calcd for C$_{28}$H$_{26}$N$_4$O$_5$Cl$_2$: C, 59.06; H, 4.60; N, 9.84; Cl, 12.45. Found: C, 59.08; H, 4.64; N, 9.82; Cl, 12.43.

What is claimed is:

1. A method for producing a phenylalanine derivative(s) having a quinazolinedione ring of the following formula (5), comprising steps of reacting an acylphenylalanine derivative(s) of formula (1):

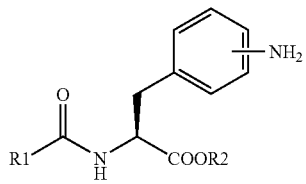

(1)

wherein R1 represents a phenyl group which may have a substituent(s) or a pyridyl group which may have a substituent(s), R2 represents an alkyl group which may have a substituent(s), and the derivative(s) is in a salt(s) with chemically acceptable acid(s) or free form(s), with a carbonyl group-introducing reagent(s) and an anthranilic acid derivative(s) of formula (2):

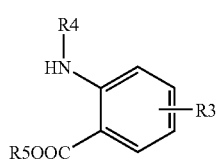

(2)

wherein R3 represents a dialkylamino group; R4 represents a hydrogen atom, an alkyl group or a benzyl group which may have a substituent(s); and R5 represents an alkyl group or an alkylcarbonyl group, and the derivative(s) is in a salt(s) with chemically acceptable acid(s) or free form(s), to form an asymmetric urea intermediate(s) of formula (3):

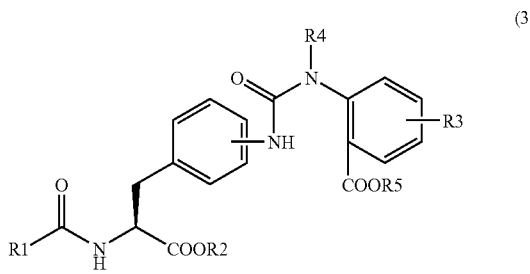

wherein R1 to R5 are defined above;
making the asymmetric urea intermediate(s) into a quinazolinedione compound(s) of formula (4) in the presence of a base(s):

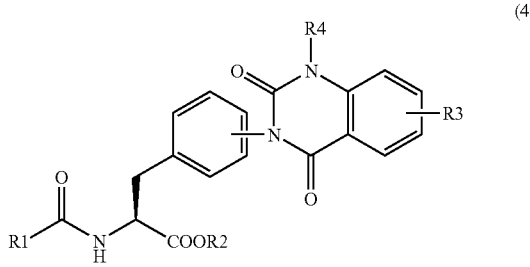

wherein R1 to R4 are defined above; and
when R4 represents a hydrogen atom in the obtained quinazolinedione compound(s) of the formula (4), N-alkylating a quinazolinedione ring amide of the quinazolinedione compound(s) with an N-alkylation agent(s) to form the phenylalanine derivative(s) having a quinazolinedione skeleton of formula (5):

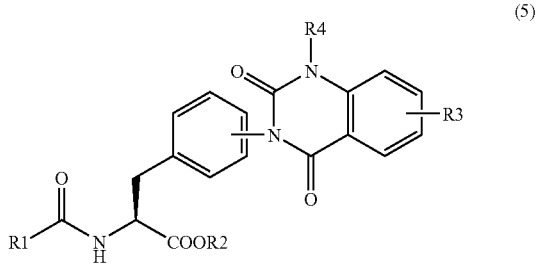

wherein R1 to R3 are defined above, R4 represents an alkyl group or a benzyl group which may have a substituent(s).

2. The production method according to claim 1, wherein the carbonyl group-introducing reagent is 1,1'-carbonyldiimidazole or chloroformate.

3. The production method according to claim 1, wherein the base(s) represents a potassium carbonate or a sodium methoxide.

4. The production method according to claim 1, wherein the N-alkylation agent is methyl p-toluenesulfonate.

5. The production method according to claim 1, comprising steps of reacting a carbonyl group-introducing reagent selected from the group consisting of 1,1'-carbonyldiimidazole and chloroformate and the compound of the formula (2) wherein R3 represents a dimethylamino group, R4 represents a hydrogen atom and R5 represents a methyl group with the compound of the formula (1) wherein R1 represents a 2,6-dichlorophenyl group and R2 represents a methyl group to obtain methylester of 2-(3-{4-[2-(2,6-dichlorobenzoylamino)-2-methoxycarbonylethyl]phenyl}ureide)-5-dimethylaminobenzoic acid; converting it in the presence of potassium carbonate or sodium methoxide into methylester of $N^\alpha$-(2,6-dichlorobenzoyl)-4-(6-dimethylamino-2,4[1H,3H]-quinazolinedione-3-yl)-L-phenylalanine of the formula (4); and then N-alkylating it with methyl p-toluenesulfonate to obtain methylester of $N^\alpha$-(2,6-dichlorobenzoyl)-4-(1-methyl-6-dimethylamino-2,4[1H,3H]-quinazolinedione-3-yl)-L-phenylalanine.

6. The production method according to claim 1 comprising steps of reacting a carbonyl group-introducing reagent selected from the group consisting of 1,1'-carbonyldiimidazole and chloroformate and the compound of the formula (2) wherein R3 represents a dimethylamino group, R4 represents a methyl group and R5 represents a methyl group with the compound of the formula (1) wherein R1 represents a 2,6-dichlorophenyl group and R2 represents a methyl group to obtain the compound of the formula (3);

converting it in the presence of potassium carbonate or sodium methoxide into methylester of $N^\alpha$-(2,6-dichlorobenzoyl)-4-(1-methyl-6-dimethylamino-2,4[1H,3H]-quinazolinedione-3-yl)-L-phenylalanine.

* * * * *